United States Patent [19]
Kyte

[11] Patent Number: 5,749,860
[45] Date of Patent: May 12, 1998

[54] DISPOSABLE SELF-CAPPING NEEDLE

[76] Inventor: Terreena Kyte, 28071 Everett, Southfield, Mich. 48076

[21] Appl. No.: 722,962

[22] Filed: Sep. 30, 1996

[51] Int. Cl.[6] .................................................. A61M 5/00
[52] U.S. Cl. ............................................. 604/192; 604/263
[58] Field of Search ................................. 604/263, 198, 604/192, 187, 110

[56] References Cited

U.S. PATENT DOCUMENTS

| | | | |
|---|---|---|---|
| 4,874,383 | 10/1989 | McNaughton | 604/198 |
| 5,002,533 | 3/1991 | Jullien | 604/192 X |
| 5,053,018 | 10/1991 | Talonn et al. | 604/198 |
| 5,279,579 | 1/1994 | D'Amico | 604/192 |
| 5,334,149 | 8/1994 | Nortman et al. | 604/110 |
| 5,336,187 | 8/1994 | Terry et al. | 604/110 |
| 5,423,756 | 6/1995 | van der Merwe | 604/110 |
| 5,433,712 | 7/1995 | Stiles et al. | 604/110 |

*Primary Examiner*—John D. Yasko
*Attorney, Agent, or Firm*—Thomas Zack; Joseph H. McGlynn

[57] ABSTRACT

A disposable self-capping needle which can be completely contained with its own sheath before and after injection takes place. The enclosing needle sheath has a protective rear seal and an openable front lid. By removing the seal a syringe can be connected to an internal needle plunger assembly to permit reciprocating needle motion within its sheath. Injection is accomplished by opening the sheath's front lid after which the needle may be completely withdrawn back into the sheath for safe disposal. Internal sheath guiding and holding grooves permit the needle's plunger assembly to reciprocate freely.

3 Claims, 1 Drawing Sheet

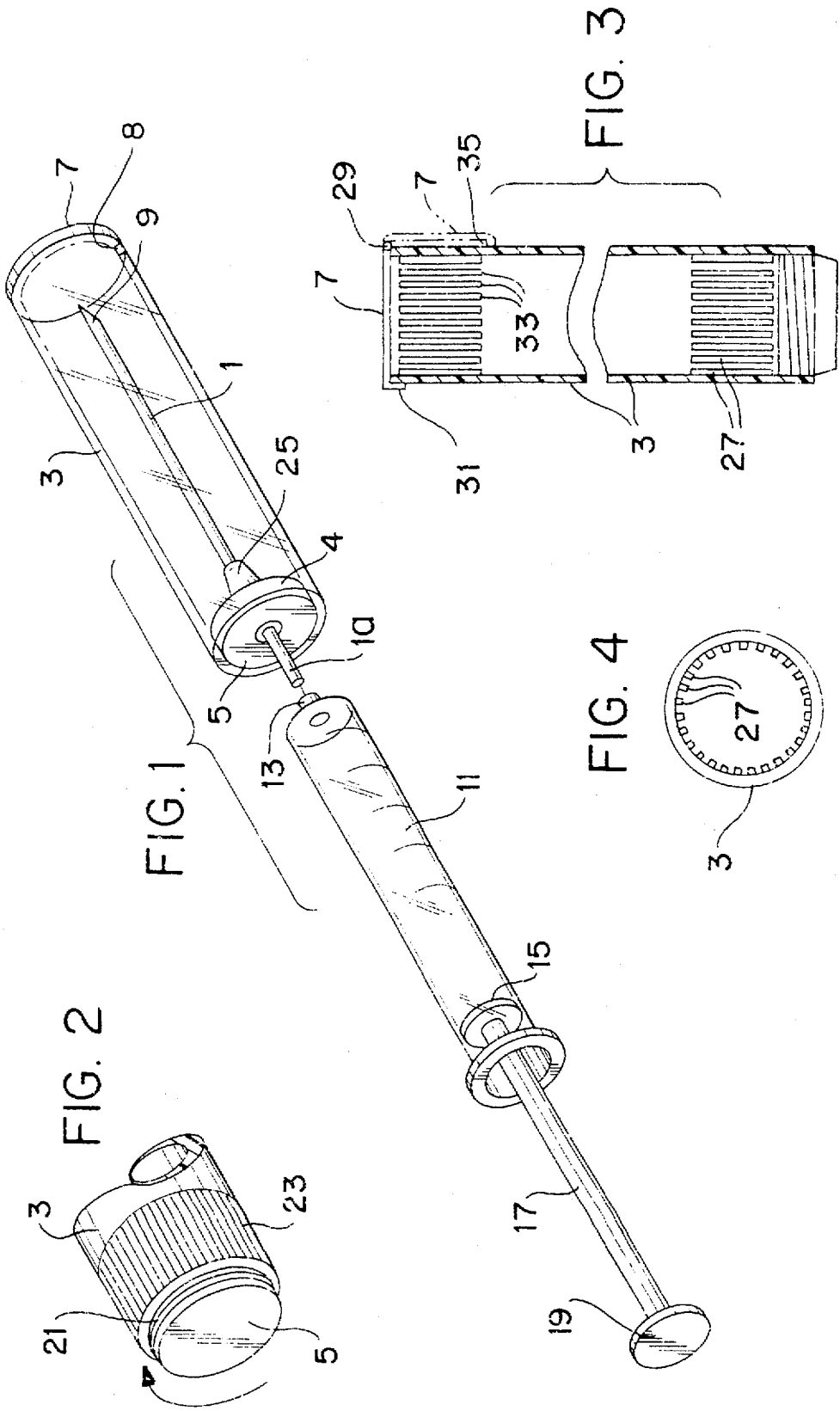

DISPOSABLE SELF-CAPPING NEEDLE

BACKGROUND OF THE INVENTION

It has long been a concern of the medical community to develop a safe disposable injection needle that will not accidentally puncture a person after it has been used. Recent health hazards relating to the acquired immune deficiency syndrome (AIDS) have exasperated this problem. Several different proposals have been suggested in the patented art to avoid this puncture danger. While not without some merit, none have suggested the needle in a sheath concept as described herein for a disposable self-capping needle.

DESCRIPTION OF THE PRIOR ART

Protective coverings for injection needles have taken many forms. For example, in U.S. Pat. No. 5,334,149 to Nortman et al., an expandable accordion shaped post-injection sheath body for the injection needle is disclosed. In the Terry et al. U.S. Pat. No. 5,336,187 a collapsible bellow shaped needle covered with a sheath is set forth. For disposable purposes, the needle and syringe in U.S. Pat. No. 5,423,756 to van der Merwe are are separated from each other. And in the U.S. Pat. No. 5,433,712 to Stiles et al. a self-sheathing needle that is irreversibly locked into the sheath is revealed. None of these references disclose or suggest a needle inside a sheath as set forth in the specification.

SUMMARY OF THE INVENTION

A needle is enclosed within a protective cap sheath having a rear protective seal and a front flip top cover. A standard syringe is mounted on the needle and sheath by breaking the protective seal. To inject or withdraw a bodily fluid, the front sheath top is withdrawn and the syringe and needle pushed forward to expose the needle's point. After this is completed, the needle is withdrawn back into its sheath and the cover moved down. The contained needle may then be safety disposed of by a user without risking accidental puncture.

It is the primary object of the present invention to provide for an improved disposable self-capping needle.

Another object is to provide for such a needle wherein the needle is completely covered by a protective sheath before and after injection takes place.

These and other objects and advantages of the present invention will become apparent to readers from a consideration of the ensuing description and the accompanying drawings.

BRIEF DESCRIPTION OF THE DRAWINGS

FIG. 1 is a perspective view of the invention's preferred embodiment.

FIG. 2 is an enlarged perspective view of the sheath's protective seal.

FIG. 3 shows a cross sectional side view of the sheath's front cap when closed and opened (shown in dotted lines).

FIG. 4 is a sheath end view showing its internal gripping grooves.

DESCRIPTION OF THE PREFERRED EMBODIMENT

FIG. 1 is a perspective view of the invention's preferred embodiment prior to using the needle for its intended purpose. A slidable hollow injection needle 1 is enclosed in the protective cap or sheath 3 both before and after the needle is used to inject or withdraw fluids from a person. A portion of the needle 1a projects from the rear of the sheath 3 to engage a tube in the syringe 11. Attached near the needle's rear end is a plunger assembly 4 which engages internal sheath grooves 33 (see FIG. 3) as the needle is reciprocated in the sheath.

Before the needle is used, the sheath's rear end is initially covered by a protective removable cap or seal 5, as shown in FIG. 2. At the sheath's front end facing toward the needle's front end is a hinged closed cap 7 (see FIGS. 1 and 3) from which the needle's injection point 9 can protrude when used. A hollow cylindrical plastic syringe 11 is used to contain the fluid either injected or withdrawn from a patient. At the syringe's front end there is a smaller diameter section 13 used to connect the needle to the rear of the syringe 1a. Within the syringe's interior a reciprocally movable plunger 15 is fitted to force the movement of fluids from or into the syringe. An elongated shaft 17 connects the syringe's plunger 15 to a thumb operated rear enlarged end 19.

FIG. 2 is an enlarged perspective view of the sheath's protective seal 5. In this view only a small part of the sheath 3 near its rear end is shown. The seal or cap 5 may be removed by twisting it relative to the sheath in the direction of the arrow to gain admittance to the sheath's hollow interior. This can be done by providing for interlocking threads in the seal's engaging end and internal threads 21 located around the sheath's rear end. External longitudinal gripping grooves 23 can be molded into the sheath's rear outer surface to facilitate holding when the seal is removed to permit twisting insertion of the syringe's front section 13 through a center hole in plunger 4 on the needle's end coupling 25 (see FIG. 1).

When the syringe is inserted into the needle's coupling 25 a series of spaced rear internal longitudinal gripping and guiding grooves 27 (see FIGS. 3) act to hold and provide a tight fit within the sheath 1 between the inserted needle's end plunger 4 and the syringe's joined front section 13. As shown in FIG. 3, the hinged cap 7 is connected by hinge 29 to the side of sheath 1. When the cap is closed its double lid catch 31 retains it in that position. A series of spaced front internal longitudinal sheath grooves 33 similar to the rear gripping grooves 27, function to grip and guide the extended plunger 4 and needle front end when the lid or cover 7 is opened. A molded side lid catch 35 on the sheath's side surface is used to retain the opened lid latched as best shown in dotted lines in FIG. 3 by engaging the catch 31.

FIG. 4 is a end view showing the sheath's internal plunger assembly gripping and guiding grooves 27. A view from the sheath's front end would reveal similar structure for the spaced internal gripping and plunger assembly guiding grooves 33.

To use the syringe and attached needle, the seal 5 is removed and the syringe 11 is connected to end 1a of the needle. The lid or cover 7 is opened and the needle's point 9 is pressed into a patient by pushing on thumb member 19 with one hand while holding the sheath 1 with the other hand. After fluid has been either injected from, or withdrawn into the syringe 11, the needle is retracted back into its sheath 1. Next, the opened lid 7 is closed, as shown in FIG. 3 to completely contain the needle and its injection point 9 within the sheath 1. Finally, the syringe and needle are safely disposed of without risk of accidental puncture to anyone.

Most of the components making up the disposable self-capping needle could be made of plastic manufactured using the plastic injection molding process. Injection molding is a plastic molding process whereby heat softened plastic material is forced under very high pressure into a metal cavity mold, usually aluminum or steel, which is relatively cool. The inside cavity of the mold is comprised of two or more halves, and is the same desired shape as the product to be formed (in this case the sheath, needle plunger and syringe components). High pressure hydraulics are used to keep the mold components together during the actual injection phase of the molding process. The injected plastic is allowed to cool and harden in the mold. The hydraulics holding the multiple component mold cavity together are released, the mold halves are separated and the solid formed plastic item is removed. Injection molding can be highly automated process and is capable of producing extremely detailed parts at a very cost effective price. The sliding needle components, including plunger 4 and the needle 1, could be made from ABS plastic and molded in place at the time the sheath part is made. The process should be invaluable in producing this invention's disposable self-capping needle cost effectively.

Although the Disposable Self-Capping Needle and the method of using the same according to the present invention has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

What I claim as my invention is:

1. A disposable self-capping needle comprising:

a hollow needle having a front exit opening and a rear plunger assembly;

a normally closed sheath completely enclosing said needle and having an openable front hinged lid end and a protective rear end seal;

means on the lid for maintaining said hinged front lid in a closed position when said lid is closed;

means on the sheath to engage said means on the lid for maintaining said hinged front lid in an opened position when said lid is opened; and a syringe capable of containing fluids and adapted to engage said needle's rear end plunger assembly when the sheath's protective rear seal does not obstruct engagement.

2. The invention as claimed in claim 1, wherein said protective seal is a threaded end cap which engages threads on said sheath.

3. The invention as claimed in claim 1, also including internal sheath spaced grooves which act to guide and hold said needle's plunger assembly when moved within said sheath.

* * * * *